(12) United States Patent
Zhang et al.

(10) Patent No.: US 11,648,540 B2
(45) Date of Patent: *May 16, 2023

(54) MODIFIED CATALYST, METHOD FOR PREPARING THE SAME, AND METHOD FOR PRODUCING AROMATIC HYDROCARBONS BY AROMATIZATION OF OLEFINS

(71) Applicants: China Energy Investment Corporation Limited, Beijing (CN); National Institute of Clean-and-Low-Carbon Energy, Beijing (CN)

(72) Inventors: Aihua Zhang, San Bruno, CA (US); Hui Wang, Fremont, CA (US); Junjun Shan, San Jose, CA (US); Joshua Miles, San Francisco, CA (US); Lisa Nguyen, Santa Clara, CA (US); Louis Guillen, San Jose, CA (US); Amin Sardar, Santa Clara, CA (US); Hua Liu, Beijing (CN)

(73) Assignees: China Energy Investment Corporation Limited, Beijing (CN); National Institute of Clean-and-Low-Carbon Energy, Beijing (CN)

( * ) Notice: Subject to any disclaimer, the term of this patent is extended or adjusted under 35 U.S.C. 154(b) by 19 days.

This patent is subject to a terminal disclaimer.

(21) Appl. No.: 17/157,563

(22) Filed: Jan. 25, 2021

(65) Prior Publication Data
US 2022/0234034 A1   Jul. 28, 2022

(51) Int. Cl.
| | | |
|---|---|---|
| *B01J 29/40* | (2006.01) | |
| *C07C 2/66* | (2006.01) | |
| *B01J 37/10* | (2006.01) | |
| *C07C 5/42* | (2006.01) | |
| *B01J 37/00* | (2006.01) | |
| *B01J 29/06* | (2006.01) | |
| *B01J 37/30* | (2006.01) | |
| *B01J 29/70* | (2006.01) | |
| *B01J 35/00* | (2006.01) | |

(52) U.S. Cl.
CPC .......... *B01J 29/405* (2013.01); *B01J 29/061* (2013.01); *B01J 29/7049* (2013.01); *B01J 35/0006* (2013.01); *B01J 37/0009* (2013.01); *B01J 37/10* (2013.01); *B01J 37/30* (2013.01); *C07C 2/66* (2013.01); *C07C 5/42* (2013.01); *B01J 2229/10* (2013.01); *B01J 2229/186* (2013.01); *B01J 2229/36* (2013.01); *B01J 2229/42* (2013.01); *C07C 2521/04* (2013.01); *C07C 2521/06* (2013.01); *C07C 2521/08* (2013.01); *C07C 2521/10* (2013.01); *C07C 2521/16* (2013.01); *C07C 2521/18* (2013.01); *C07C 2523/08* (2013.01); *C07C 2523/10* (2013.01); *C07C 2529/40* (2013.01); *C07C 2529/70* (2013.01); *C10G 2300/703* (2013.01); *C10G 2400/30* (2013.01)

(58) Field of Classification Search
CPC .... B01J 29/405; B01J 29/061; B01J 29/7049; B01J 2229/10; B01J 2229/186; B01J 2229/36; B01J 2229/42; B01J 37/0009; B01J 37/10; B01J 37/30; B01J 35/0006; C07C 2529/40; C07C 2529/70; C07C 2523/08; C07C 2523/10; C07C 2521/04; C07C 2521/06; C07C 2521/08; C07C 2521/10; C07C 2521/16; C07C 2521/18; C10G 2400/30; C10G 2300/703
USPC ... 502/60, 61, 63, 64, 65, 68, 69, 71, 73, 77
See application file for complete search history.

(56) References Cited

U.S. PATENT DOCUMENTS

| | | | |
|---|---|---|---|
| 5,968,342 A * | 10/1999 | Tsunoda ................. | C10G 11/05 502/64 |
| 8,946,107 B2 | 2/2015 | Lauritzen et al. | |
| 10,087,124 B2 | 10/2018 | Hong | |
| 10,596,558 B2 * | 3/2020 | Arvind .................... | C10G 35/14 |
| 11,192,094 B2 * | 12/2021 | Rownaghi .............. | B33Y 10/00 |
| 11,273,430 B2 * | 3/2022 | Wang ....................... | B01J 29/44 |

* cited by examiner

*Primary Examiner* — Elizabeth D Wood
(74) *Attorney, Agent, or Firm* — Calfee, Halter & Griswold LLP

(57) ABSTRACT

The present disclosure provides a modified catalyst, and preparation method and a method for producing aromatic hydrocarbons by aromatization of olefins using the modified catalyst. The modified catalyst comprises an acidic molecular sieve and an olefin aromatization active metal component, the total acid amount of the catalyst as measured by $NH_3$-TPD method is not higher than 0.35 mmol/g, and ratio of the strong acid to weak acid is within a range of 0.8-1.2.

8 Claims, 6 Drawing Sheets

MODIFIED CATALYST, METHOD FOR PREPARING THE SAME, AND METHOD FOR PRODUCING AROMATIC HYDROCARBONS BY AROMATIZATION OF OLEFINS

FIELD

The present disclosure relates to the technical field of producing aromatic hydrocarbons, and particularly relates to a modified catalyst and a preparation method thereof, and a method for producing aromatic hydrocarbons by aromatization of olefins using the modified catalyst.

BACKGROUND

Directly converting light alkanes into aromatic hydrocarbon compounds has been one of the major interests for academia and industry. Over the past decades, Shell Oil, Exxon Mobil, Saudi Basic Industries Corporation (SABIC) and other individual inventors have been granted or currently applying patents worldwide related to the technologies. From the perspective of the chemical reaction mechanism, the conversion from ethane to aromatic hydrocarbons needs to go through a step with ethylene as an intermediate product. That is, ethane first needs to be dehydrogenated and activated to the intermediate ethylene which has high reactivity. Then the ethylene is oligomerized/aromatized on the acid sites to convert into the aromatic hydrocarbon compounds and the like. The dehydrogenation usually requires a dehydrogenation function from noble metals such as platinum (Pt) and palladium (Pd), and oligomerization/aromatization is usually performed on a zeolite catalyst such as ZSM-5.

Therefore, the direct conversion of ethane to aromatic products by a one-step process needs to be performed in the presence of a bifunctional catalyst. However, due to the limit of thermodynamic, high temperature is required for alkane dehydrogenation, ideally above 750° C. for ethane. On the other side, the olefin aromatization reaction catalyzed by ZSM-5 molecular sieve is an exothermic process, it takes place in an appropriate temperature range of 400-500° C., further higher temperature will inevitably result in fast catalyst deactivation due to coking and significant high amount of cracking product, methane.

In view of this reason, the current one-step process development is typically selected within the temperature range of 550-650° C., which is obviously a compromised option, considering the two-step reaction conditions. Under such a temperature condition, the conversion rate of ethane is limited, with a maximum equilibrium conversion rate from ethane to ethylene less than 30%, but this temperature is already excessively high for the molecular sieve catalyzed conversion between hydrocarbons, as the carbon deposition and byproduct formation are severe.

The main defect of the one-step process in terms of product composition is the very high selectivity of the pyrolysis product, methane and the heavy fractions (generally referred to the aromatic hydrocarbon fractions with the number of carbon atoms greater than 10), resulting in low carbon utilization. For example, in U.S. Pat. No. 8,946, 107B2, Shell Oil discloses a process for the conversion of ethane to aromatic hydrocarbons, the initial conversion rate of $C_2H_6$ obtained at 630° C., 1000 GHSV with Pt—Fe/ZSM-5 catalysts is 50-60%, the total aromatic hydrocarbon selectivity is within a range of 53-65%, while methane selectivity could be as high as 41%, and methane selectivity can be reduced to 24% by adding 0.08% Fe, but the ethane conversion is reduced by about 10% at the same time. As another example, U.S. Pat. No. 10,087,124 discloses ethane aromatization results obtained from a fluidized bed reactor at 540-560° C. with a WHSV of 1.0 g-$C_2H_6$/g-cat.hr, the average ethane conversion rate over three cycle lifetime runs is only around 30%, total aromatic hydrocarbon selectivity (A6+) is close to 70%, whereas the heavy aromatic hydrocarbon fractions (A10+) are close to 20% out of total carbon base products and approaching to 30% out of total aromatic products, thereby causing loss of the carbon base feedstock.

Another disadvantage of bifunctional catalysts used in the one-step process is that the noble metal such as Pt would easily migrate and sinter at high temperature, and regeneration after several cycles becomes increasingly difficult and the catalyst activity is decreased accordingly.

SUMMARY

In view of the aforementioned problems in the prior art, the inventors of the present disclosure have proposed in the previous patent document CN201911156645.3 that alkane conversion and selectivity can be easily adjusted by separating dehydrogenation from oligomerization/aromatization and performing the reactions in two steps, and it is not required to use a noble metal catalyst, thereby making it possible to significantly reduce the catalyst cost. Wherein the dehydrogenation may be a thermochemical reaction, or be performed in the presence of a dehydrogenation catalyst such as a noble metal, and the aromatization is performed in the presence of a zeolite molecular sieve. In order to further improve carbon utilization rate and increase production of aromatic hydrocarbons in a single cycle, and extend the single-cycle service life and multi-cycle stability of the catalyst, the inventors have further proposed in CN202010265633.0 to use zeolite molecular sieve (e.g., ZSM-5) modified by a metal such as Ga as an aromatization catalyst. For the sake of further improving economical efficiency of the two-step process, the inventors of the present disclosure have conducted continuous research on the technology, thereby completing the present disclosure.

The object of the present disclosure is to provide a modified catalyst and a method for modifying catalyst and a method for producing aromatic hydrocarbons by dehydrogenation and aromatization of light hydrocarbons using the modified catalyst, so as to further improve the economical efficiency of producing aromatic hydrocarbons through dehydrogenation and aromatization of light hydrocarbons in a two-step process, increase BTX product yield and extend cycle life of the catalyst.

In order to achieve the above objects, a first aspect of the present disclosure is to provide a modified catalyst comprising an acidic molecular sieve and an olefin aromatization active metal component, wherein the total acid amount of the catalyst as measured by $NH_3$-TPD method is not higher than 0.35 mmol/g, and ratio of the strong acid to weak acid is within a range of 0.8-1.2.

In a second aspect, the present disclosure provides a method for modifying a catalyst, the method comprises subjecting a catalyst containing an acidic molecular sieve and an olefin aromatization active metal component to a steaming treatment by introducing the flowing steam, the conditions of steaming treatment reduce the acid amount of the catalyst by 30-70%.

Preferably, the catalyst containing the acidic molecular sieve and the olefin aromatization active metal component is placed in a tube the tube is then introduced with flowing steam or a mixed stream of flowing steam and an inert gas, so as to bring the catalyst into uniform and sufficient contact with the steam for performing the steaming treatment.

In a third aspect, the present disclosure provides a method for producing aromatic hydrocarbons by aromatization of olefins, the method comprises the following steps:

1) preparing an aromatization catalyst using the aforementioned method;

2) contacting the olefin-containing feedstock with the aromatization catalyst obtained in step 1) under the aromatization reaction conditions to perform an oligomerization/aromatization reaction to obtain a material flow comprising aromatic hydrocarbons.

The present disclosure can effectively reduce production of low economic value components such as methane, the fractions of A10+ while ensuring conversion rate of olefins by producing aromatic hydrocarbons through dehydrogenation and aromatization of light hydrocarbons using a modified catalyst having a lower total acid amount and a substantially constant ratio of strong acid to weak acid, it may not only increase yield of the high economic value product BTX, but also effectively extend the cycle life of the catalyst.

The present disclosure not only improves the performance of the catalyst by subjecting the catalyst containing an acidic molecular sieve and an olefin aromatization active metal component to a steaming treatment with flowing steam or flowing steam and an inert gas, but also the concept and practice of the flow process of the present disclosure have proven that the scale may be magnified, which guarantees effectiveness of the treatment and uniformity of the material; however, the conventional steam aging process does not guarantee effectiveness of the treatment and uniformity of the material, and the large-scale production is limited, as the static steam only have an effective contact with surface parts of the molecular sieve.

The catalysts provided by the present disclosure have significantly reduced methane and ethane selectivity, higher BTX product selectivity and longer single cycle lifetime of the catalysts as compared to the Ga/ZSM-5 catalyst which is not subjected to a steaming treatment.

BRIEF DESCRITION OF THE DRAWINGS

FIG. 1 shows the results of ammonia temperature programmed desorption ($NH_3$-TPD) for several catalysts.

FIGS. 2A-2D illustrate the cycle lifetime results obtained for Examples 5, 6, 7 and Comparative Example 4 at 500° C., 3 bar, WHSV=1.5 g-$C_2H_4$/g-cat.hr, and the gas feedstock comprised of $C_2H_6$:$C_2H_4$:$H_2$:$N_2$ in 0.67:1:1:1 (volume ratio), wherein FIG. 2A shows the ethylene conversion rate, FIG. 2B illustrates the liquid product ($C_6^+$) yield, FIG. 2C illustrates the ethylene conversion rate versus methane selectivity, FIG. 2D shows breakdown of the aromatic hydrocarbon fractions.

Figure 1:
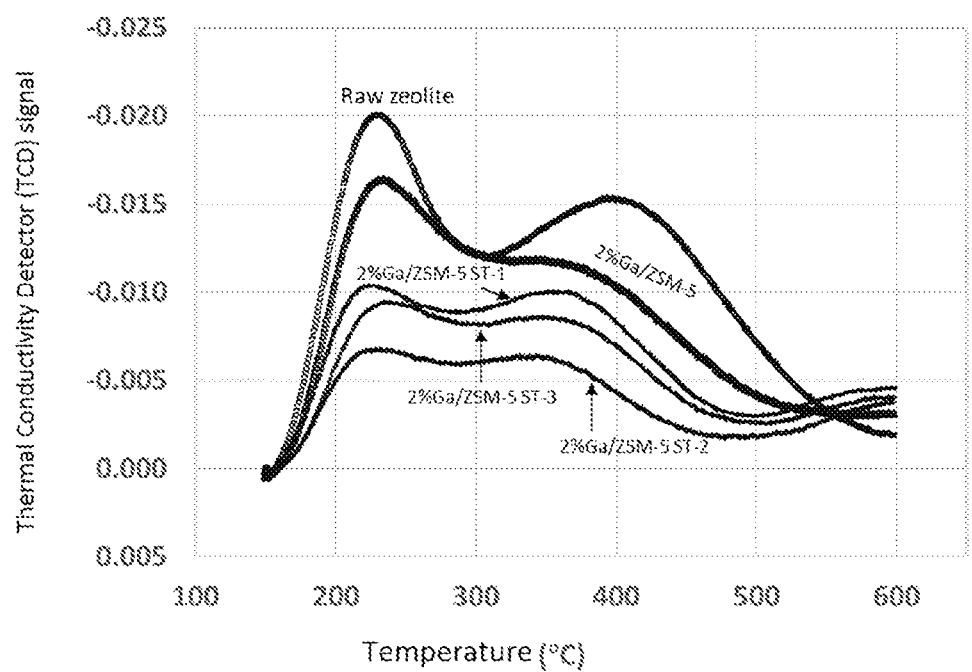

In addition, each of the amounts mentioned in the text and the figures and tables are on the basis of molar amounts of carbon.

DETAILED DESCRIPTION

The terminals and any value of the ranges disclosed herein are not limited to the precise ranges or values, such ranges or values shall be comprehended as comprising the values adjacent to the ranges or values. As for numerical ranges, the endpoint values of the various ranges, the endpoint values and the individual point value of the various ranges, and the individual point values may be combined with one another to produce one or more new numerical ranges, which should be deemed have been specifically disclosed herein.

The present disclosure provides a catalyst, wherein the total acid amount of the catalyst as measured by $NH_3$-TPD method is not higher than 0.35 mmol/g, and ratio of the strong acid to weak acid is within a range of 0.8-1.2.

According to a preferred embodiment of the present disclosure, the total acid amount of the modified catalyst is 0.1-0.3 mmol/g, and ratio of the strong acid to weak acid is within a range of 0.9-1.1. Preferably, in order to further improve the aromatization properties of the catalyst, the strong acid amount of the catalyst is approximately equal to the weak acid amount. Preferably, the strong acid amount of the catalyst is within a range of 0.05-0.2 mmol/g, preferably 0.06-0.15 mmol/g; and the weak acid amount is within a range of 0.05-0.2 mmol/g, preferably 0.06-0.15 mmol/g. Preferably, the catalyst has an ammonia desorption temperature lower than 370° C., preferably 340-365° C. at the strong acid site of the modified catalyst, and an ammonia desorption temperature lower than 235° C., preferably 220-230° C. at the weak acid site.

The total acid amount of the catalyst referred in the present disclosure is measured by the ammonia temperature programmed desorption ($NH_3$-TPD) method and is calculated based on the desorption curves. The amount of acid having a peak temperature value lower than 300° C. is defined as the weak acid amount; the amount of acid having a peak temperature value not lower than 300° C. is defined as the strong acid amount. The specific test method is as follows: about 0.2 g of a catalyst sample is weighted, and loaded into a quartz sample tube, which is placed in a heating furnace. The helium (He) gas is used as a carrier gas, the catalyst sample is heated to 550° C., and purged at a flow rate of 25 ml/min for 60 min to remove impurities adsorbed on surface of the catalyst. The catalyst is then cooled to 100° C., and $NH_3$—He mixed gas (10% $NH_3$+90% He) is introduced for 80 min to reach the saturated adsorption, and subsequently purged with He gas for 20 min till the baseline is stable, so as to desorb the physically adsorbed ammonia. Finally, the temperature is raised to 600° C. at a temperature rise rate of 10° C./min so as to carry out the ammonia desorption, and the desorption curve is recorded by a Thermal Conductivity Detector (TCD), and the data processing is implemented with a program attached on the instrument, such that the strong acid amount, weak acid amount, total acid amount, ammonia desorption temperature at strong acid site and ammonia desorption temperature at weak acid site are calculated.

The types and the amounts of the acidic molecular sieve and the olefin aromatization active metal component of the present disclosure can be appropriately selected with reference to the content disclosed by the inventors of the present disclosure in the foregoing patent documents, preferably the acidic molecular sieve is a molecular sieve with a MFI structure, more preferably ZSM-5; the olefin aromatization active metal component is one or more selected from the group consisting of Ga, Zn and Sn, wherein Ga is particularly preferred.

The Silica-Alumina molar Ratio (SAR) of ZSM-5 molecular sieve may be within a range of 20-400, more preferably 30-80.

Preferably, the weight ratio of the acidic molecular sieve and the olefin aromatization active metal component in the catalyst is 1:0.001-0.1, preferably 1:0.005-0.05.

Preferably, the content of the olefin aromatization active metal component is 0.5-10 wt %, more preferably 1-5 wt %, based on the total amount of catalyst.

According to a preferred embodiment of the present disclosure, the catalyst further comprises a binder in an amount of 10-40 wt %, preferably 15-25 wt % based on the total amount of the catalyst.

Preferably, the binder is one or more selected from the group consisting of silica, alumina, silicon carbide, clay, ceria, lanthana, magnesium oxide, titanium oxide and zirconia.

According to a second aspect, the present disclosure provides a method for modifying a catalyst, the method comprises subjecting a catalyst containing an acidic molecular sieve and an olefin aromatization active metal component to a steaming treatment by introducing the flowing steam or a mixture of water steam and an inert gas, the conditions of steaming treatment reduce the acid amount of the catalyst by 30-70%.

The present inventors have discovered that controlling the acid amount loss of the catalyst by about 30-70% may inhibit formation of byproducts such as methane, thereby increasing the overall carbon utilization rate (the sum of A6-A9 and C2-05 hydrocarbons), and greatly extending the single cycle lifetime of the catalyst. The reason may be that the portion of removed acid primarily serves to catalyze some side reactions such as hydrocracking, which is the main route of generating the by-products such as methane. By subjecting a catalyst comprising an acid molecular sieve and an olefin aromatization active metal component to a steaming treatment with the flowing steam and the flowing inert gas, the appropriate acid amount, the adequate acid strength, and the suitable strong acid to weak ratio can be obtained.

Excessive decline of the acid amount may lead to a reduction in the overall activity of the catalyst; too small decline of the acid amount will not significantly improve the catalyst performance.

The steaming treatment of the present disclosure has at least the following differences compared to the conventional hydrothermal aging: 1) the former is carried out in an inert gas or air atmosphere using flowing water steam, while the latter is typically treated with static water steam in a closed reactor; 2) the intake amount of steam and inert gas and the introduction time period are closely related to the reduction of the acid amount and must be strictly controlled.

In the present disclosure, the flowing water steam can make the acid amount of the catalyst to be decreased in the sufficient, uniform and controllable manner. The introduction of an inert gas (also including air) serves to enhance the disturbance effect, and in combination with the intake amount of water steam, the contact time and the like, in order to guarantee the sufficient contact between the water steam and the catalyst, thereby ensuring the effectiveness and uniformity of the steaming treatment.

According to a preferred embodiment of the present disclosure, the conditions of steaming treatment include that the temperature is within a range of 200-800° C., the time is 1-10 hours, the intake amount of steam is 0.1-3 g/g cat.hr, the intake amount of the inert gas is 0.1-3 g/g cat.hr; preferably the temperature of steaming treatment is within a range of 450-600° C., the time is 2-8 hours, the intake amount of steam is 0.3-1.5 g/g cat.hr, the intake amount of the inert gas is 0.5-1.5 g/g cat.hr.

Further preferably, the ratio of the intake amount of steam to the intake amount of the inert gas on a mass basis is 1:0.2-2, preferably 1:0.5-1.5.

In the present disclosure, the inert gas may be various gases which do not adversely affect the catalyst performance and the steaming treatment process, such as nitrogen, air, and a gas of a group 0 element from the periodic table of elements.

The method of the present disclosure is applicable to a wide variety of catalysts containing an acidic molecular sieve and an olefin aromatization active metal component.

Preferably, the catalyst has a weight ratio of the acidic molecular sieve and the olefin aromatization active metal component being 1:0.001-0.1.

Preferably, the acidic molecular sieve has a Silica-Alumina molar Ratio (SAR) within a range of 20-400, more preferably 30-80.

In the present disclosure, the acidic molecular sieve may be various molecular sieves useful in the technical field of converting light hydrocarbons to aromatic hydrocarbons, preferably the acidic molecular sieve is a zeolite molecular sieve having a MFI or MEL structure, such as at least one selected from the group consisting of ZSM-5, ZSM-8, ZSM-11, ZSM-12, ZSM-23 and ZSM-35, further preferably ZSM-5.

Preferably, the olefin aromatization active metal component is one or more selected from the group consisting of Ga, Zn and Sn, wherein Ga is particularly preferred.

According to a preferred embodiment of the present disclosure, the catalyst further comprises a binder in an amount of 10-40 wt %, preferably 15-25 wt % based on the total amount of the catalyst.

The binder may be any of a variety of materials capable of binding the molecular sieve particles together into a molded form, preferably an inorganic refractory oxide commonly used in the catalyst field, more preferably one or more selected from the group consisting of silica, alumina, silicon carbide, clay, ceria, lanthana, magnesium oxide, titanium oxide and zirconia.

Preferably, the molecular sieve has a Silica-Alumina molar Ratio (SAR) within a range of 23-400, preferably 30-80.

The catalyst provided in the present disclosure can be in powder form or the molded form of trilobe, strip-type, column-shape, spherical shape. In order to avoid generation of a pressure drop in the reactor tube and facilitate the recycling and regeneration, it is preferred that the catalyst is in the aforementioned molded form.

Preferably, the catalyst further comprises a binder in an amount of 10-40 wt %, preferably 15-25 wt % based on the total amount of the catalyst.

In the present disclosure, the catalyst comprising an acidic molecular sieve and an olefin aromatization active metal component can be prepared by a wet impregnation method or a dry mixing and kneading method comprising initially loading the olefin aromatization active metal component onto the acidic molecular sieve or onto the acidic molecular sieve and a binder (if any), then molding (if a binder is presented), and subsequently subjecting to the drying and calcining process.

The impregnation method may be a saturation impregnation process, or an unsaturated impregnation process, or an equal volume impregnation process, as long as the metal elements are loaded onto the acidic molecular sieve.

In the present disclosure, the solvent brought about by the impregnation method is removed by drying. Preferably, the drying conditions include a temperature of 60-120° C.

The calcining process is performed after the drying process. Preferably, the calcining conditions include a temperature of 450-700° C., preferably 500-650° C., and a time of 3-15 hours, preferably 5-12 hours.

According to a third aspect, the present disclosure provides a method for producing aromatic hydrocarbons by aromatization of olefins, the method comprises the following steps:

1) modifying the aromatization catalyst using the aforementioned method.

2) contacting the olefin-containing feedstock with the aromatization catalyst obtained in step 1) under the aromatization reaction conditions, so as to carry out an oligomerization/aromatization reaction to obtain a material flow comprising aromatic hydrocarbons.

The method for preparing a modified aromatization catalyst of step 1) has been described in the above text.

Preferably, the aromatization reaction conditions comprise that the temperature is within a range of 350-650° C., and the olefin-containing feedstock has a gas hourly space velocity (GHSV) of 500-20000 $h^{-1}$, preferably 800-5000 $h^{-1}$.

Preferably, the contacting conditions include: a pressure in term of the gauge pressure is within a range of 0.01 MPa-2 MPa; a temperature is within a range of 300-700° C., preferably 400-600° C.; and the olefin-containing feedstock has a GHSV of 500 $h^{-1}$-50000 $h^{-1}$, preferably 1000 $h^{-1}$-10000 $h^{-1}$.

Preferably, said contacting is implemented in a fixed bed reactor, a fluidized bed reactor or a moving bed reactor.

The method of the present disclosure is applicable to a wide variety of olefin materials capable of subjecting to the oligomerization/aromatization to produce aromatic hydrocarbons, preferably the olefins have a number of carbon atoms from 2 to 5, such as one or more selected from the group consisting of ethylene, propylene and butylene, more preferably ethylene.

Preferably, the olefin content in the olefin-containing feedstock is within a range of 10-40% by volume, more preferably 20-30% by volume.

Preferably, the olefin-containing feedstock further contains hydrogen gas and a diluent gas such as nitrogen gas, more preferably, the volumetric ratio of olefin:hydrogen gas:nitrogen gas is within the range of 1:0.5-1.5:0.5-2, for example 1:1:1.67.

The olefin-containing feedstock may be obtained in various ways, such as by directly mixing according to the above-mentioned ratio, or by dehydrogenation of the alkane. The experiments have demonstrated that the composition of the product stream obtained in the alkane dehydrogenation step of a two-step process generally further comprises the unconverted alkane. The inventors of the present disclosure have discovered that the alkane therein may replace nitrogen gas as a diluent gas. In order to favorably simulate the two-step alkane dehydrogenation process for preparing aromatic hydrocarbons, the olefin-containing feedstock typically contains olefin, alkane, hydrogen gas and nitrogen gas, wherein the volume ratio of olefin:hydrogen gas:nitrogen gas:alkane is within the range of 1:0.5-1.5:0.5-1.5:0.5-1, e.g. 1:1:1:0.67. Furthermore, the alkane replacing a part of nitrogen gas as a diluent gas is also slightly conducive to the aromatization reaction.

Therefore, according to a preferred embodiment of the present disclosure, the method for dehydrogenation and aromatization of light hydrocarbons to produce aromatic hydrocarbons comprises the following steps:

1) preparing a modified aromatization catalyst;

2) subjecting the light hydrocarbon feedstock to a dehydrogenation reaction under the dehydrogenation reaction conditions to obtain an olefin-containing feedstock;

3) contacting the olefin-containing feedstock with the aromatization catalyst obtained in step 1) under the aromatization reaction conditions to perform an oligomerization/aromatization reaction to obtain a material flow comprising aromatic hydrocarbons.

In the above process for preparing aromatic hydrocarbons from light hydrocarbons, the light hydrocarbons are subjected to a series of reactions such as dehydrogenation, oligomerization and aromatization sequentially to obtain the aromatic hydrocarbons.

The specific operations and conditions of the dehydrogenation reaction in step 2) and the aromatization reaction in step 3) may be referred to the content described in the patent documents previously filed by the inventors of the present disclosure.

In the present disclosure, the dehydrogenation reaction can be carried out in the presence of a dehydrogenation catalyst or in the absence of a dehydrogenation catalyst.

The dehydrogenation catalyst may be various catalyst having an alkane dehydrogenation function, and preferably, the dehydrogenation catalyst is a supported catalyst comprising a carrier and a metal component having a dehydrogenation activity supported on the carrier. The carrier is an inorganic heat-resistant oxide having no acidic centers Preferably, the metal component having dehydrogenation activity is a noble metal component, such as Pt and/or Pd.

According to one embodiment of the present disclosure, the metal component having dehydrogenation activity is present in an amount of 0.01-2.0 wt %, preferably 0.02-0.2 wt %, based on the total amount of the dehydrogenation catalyst.

Preferably, the carrier is one or more selected from the group consisting of silica, alumina, silicon carbide, clay, ceria, lanthana, magnesium oxide, titanium oxide and zirconia.

The carrier is present in an amount of 98-99.99 wt %, preferably 99.8-99.98 wt %.

The above-mentioned catalysts may be commercially available or be prepared through the known methods.

As mentioned above, given that the dehydrogenation reaction is carried out independently in the present disclosure, the dehydrogenation reaction may be performed under conditions which are conducive to dehydrogenation. Preferably, when the dehydrogenation reaction is carried out in the presence of a dehydrogenation catalyst, the dehydrogenation reaction is performed at a temperature lower than 900° C., preferably within a range of 650-850° C. The temperature is below the typical ethane cracking reaction temperature (generally higher than 850° C.).

Preferably, the material flow of light hydrocarbons has a GHSV within the range of 500-20000 $h^{-1}$, preferably 800-5000 $h^{-1}$.

According to another embodiment of the present disclosure, the dehydrogenation reaction is carried out in the absence of said dehydrogenation catalyst, and the temperature of the dehydrogenation reaction is preferably within a range of 700-900° C. The reactant residence time is preferably within a range of 0.05-30 seconds. In the present disclosure, the reactant residence time means the time during which the reactants are maintained at the above-mentioned dehydrogenation reaction temperature within a range of 700-900° C., i.e. the time of dehydrogenation reaction.

In order to reduce the partial pressure of the alkane to facilitate conversion of the light hydrocarbons, a diluent is preferably fed into the dehydrogenation reactor. For example, the diluent may be an inert gas such as nitrogen, which does not adversely affect the reaction.

Since step 1) of the present disclosure aims to dehydrogenate the light hydrocarbons with the corresponding olefin as the desired product, thus the target of said dehydrogenation reaction is to obtain more olefin as far as possible, the product of dehydrogenation reaction is called as an "olefin-containing feedstock". The olefin-containing feedstock can be directly subjected to the oligomerization/aromatization reaction of step 2) without separation, such an arrangement may skip the steps of cooling and separation and reheating to reach the temperature required for the oligomerization/aromatization reaction, shorten the process flow, thereby significantly cutting the costs associated therewith. Therefore, it is preferable that the olefin-containing feedstock is not subjected to separation but directly subjecting to the oligomerization/aromatization reaction of step 2).

In the present disclosure, the oligomerization/aromatization reaction of step 2) refers to a reaction that the olefin-containing feedstock obtained by dehydrogenation of step 1) is subjected to oligomerization and aromatization to form aromatic hydrocarbons.

According to the present disclosure, the hydrocarbons in the light hydrocarbon feedstock may be various substances capable of undergoing a dehydrogenation reaction as well as the oligomerization/aromatization reaction to produce aromatic hydrocarbons, such as alkanes having a number of carbon atoms not exceeding 5. Preferably, the content of ethane in the light hydrocarbon feedstock is not lower than 65 wt %, preferably 75-100 wt %.

Preferably, the olefin-containing feedstock has an ethylene content not lower than 10% by volume, preferably 20-40% by volume.

Preferably, the olefin-containing feedstock is directly subjected to the oligomerization/aromatization reaction of step 2) without separation.

Preferably, the aromatization reaction conditions comprise that the temperature is within a range of 350-650° C., and the olefin-containing feedstock has a GHSV of 500-20000 $h^{-1}$, preferably 800-5000 $h^{-1}$.

Preferably, the contacting conditions include: a pressure in term of the gauge pressure is within a range of 0.01 MPa-2 MPa; a temperature is within a range of 300-700° C., preferably 400-600° C.; and the olefin-containing feedstock has a GHSV of 500 $h^{-1}$-50000 $h^{-1}$, preferably 1000 $h^{-1}$-10000 $h^{-1}$.

Preferably, said contacting is implemented in a fixed bed reactor, a fluidized bed reactor or a moving bed reactor.

The method of the present disclosure can be used in a wide variety of hydrocarbon materials capable of undergoing dehydrogenation reaction and oligomerization/aromatization reaction to produce aromatic hydrocarbons, preferably the light hydrocarbons are alkanes a number of carbon atoms not exceeding 5, such as ethane, propane, butane, pentane and various isomers thereof. Preferably, the content of ethane in the light hydrocarbons is not lower than 65 wt %, preferably 75-100 wt %.

As previously mentioned, the use of said catalyst provided by the present disclosure may increase yield of aromatic hydrocarbons, especially BTX, improve carbon utilization rate, and significantly extend the cycle life of the catalyst.

The present disclosure will be described in detail with reference to examples. In the following examples, the content of active metal elements in the catalyst was measured by an X-ray fluorescence spectroscopy instrument using an X-ray fluorescence spectroscopic method.

The desorption curve of ammonia on the catalyst was determined using the ammonia temperature programmed desorption ($NH_3$-TPD) method described above and a Micromeritics AutoChem II2920/AutoChem HP2950 Chemisorber instrument; in addition, the amount of acid contained in the catalyst, including the weak acid amount, the strong acid amount, the total acid amount, and the desorption temperature of ammonia at the strong acid site and the weak acid site (desorption temperature) were calculated based on the desorption curve.

Catalyst performance test: the catalyst was loaded into an ½"quartz or alumina or stainless steel (SS) tube reactor. The reaction temperature was 450-630° C. and the reaction pressure was ambient pressure to 5 bar. The feedstock gas, depending on the target object to be tested, may be a) simple feedstock gas consisting of $C_2H_4$, $H_2$ and $N_2$ in a ratio of 1:1:1 or 1:1:1.67 (volume ratio), or b) the simulated product from the dehydrogenation of ethane at 750° C. in the two-step process, usually containing $C_2H_6$, $C_2H_4$, $H_2$ and $N_2$ in a volume ratio of 0.67:1:1:1. All products were analyzed either entirely online, or online in regard to the gases and off-line in regard to the liquids by using Gas Chromatography (GC) system manufactured by the Agilent Technologies Inc. The reaction data could be collected (a) for the first few hours such as 6 hours, or (b) for a single cycle lifetime until the catalyst is deactivated.

Preparation examples 1-6

Preparation examples 1 and 5 (preparation of base catalyst): Ga-modified ZSM-5 was prepared through a wet impregnation method, ZSM-5 was mixed with pseudo-boehmite as a binder, the gallium nitrate solution was blended with water to form a paste, and then subjected to extrusion molding, drying and then calcining. The calcined product was subsequently crushed and sieved, and the 20-40 mesh product was ready for use as the base catalysts, 2% Ga/ZSM-5, 4% Ga/ZSM-5.

Preparation examples 2, 3, 4 and 6 (steaming treatment): 20-40 mesh base catalyst was placed in a tube furnace, and subjected to steaming treatment under the condition of continuously introducing water steam and nitrogen gas to obtain the steaming treated catalysts 2% Ga/ZSM-5 ST-1, 2% Ga/ZSM-5 ST-2, 2% Ga/ZSM-5 ST-3 and 4% Ga/ZSM-5 ST-3, respectively.

The specific conditions for Preparation examples 1-6 were as shown in Table 1 below.

TABLE 1

|  |  | Preparation example 1 | Preparation example 2 | Preparation example 3 | Preparation example 4 | Preparation example 5 | Preparation example 6 |
|---|---|---|---|---|---|---|---|
|  |  | Number of catalysts | | | | | |
|  |  | 2% Ga/ZSM-5 | 2% Ga/ZSM-5 ST-1 | 2% Ga/ZSM-5 ST-2 | 2% Ga/ZSM-5 ST-3 | 4% Ga/ZSM-5 | 4% Ga/ZSM-5 ST-3 |
| Preparation of base catalysts | Ga (wt %) | | | 2 | | | 4 |
|  | Binder (wt %) | | | 20 | | | 20 |
|  | ZSM-5 SAR | | | 30 | | | 30 |
|  | Calcination temperature (° C.) | | | 600 | | | 600 |
|  | Calcination time (hours) | | | 10 | | | 10 |
| Steaming treatment | Temperature (° C.) | None | 475 | 550 | 550 | None | 550 |
|  | Time (hours) | | 4 | 6 | 3 | | 3 |
|  | Steam (g/g cat.hr) | | 0.5 | 0.75 | 0.5 | | 0.5 |
|  | Nitrogen gas (g/g cat.hr) | | 0.75 | 0.5 | 0.75 | | 0.75 |

The acid amount of the catalysts was tested using $NH_3$-TPD. The results were shown in FIG. 1 and Table 2 below.

TABLE 2

| Samples | Ammonia desorption temperature (° C.) | | Acid amount (mmol/g-cat) | | | Strong/ weak | Acid amount loss, % |
|---|---|---|---|---|---|---|---|
|  | Weak acid | Strong acid | Weak acid amount | Strong acid amount | Total acid amount | | |
| Raw ZSM-5 * | 223.6 | 396.4 | 0.250 | 0.334 | 0.584 | 1.33 | Base |
| 2% Ga/ZSM-5 | 229.1 | 376.2 | 0.247 | 0.188 | 0.435 | 0.76 | 6.91% |
| 2% Ga/ZSM-5 ST-1 (475° C., 4 hrs) | 220.2 | 360.8 | 0.122 | 0.132 | 0.254 | 1.09 | 45.73% |
| 2% Ga/ZSM-5 ST-2 (550° C., 6 hrs) | 223.3 | 347.6 | 0.077 | 0.077 | 0.154 | 0.99 | 67.08% |
| 2% Ga/ZSM-5 ST-3 (550° C., 3 hrs) | 229.4 | 359.4 | 0.104 | 0.094 | 0.198 | 0.90 | 57.65% |
| 4% Ga/ZSM-5 | 229.2 | 376.8 | 0.235 | 0.205 | 0.440 | 0.87 | 5.89% |
| 4% Ga/ZSM-5 ST-3 (550° C., 3 hrs) | 229.0 | 358.6 | 0.110 | 0.100 | 0.210 | 0.91 | 55.08% |

* acid amount is pure zeolite based.

The results of FIG. 1 and Table 2 indicated that the steaming treatment caused a 45-70% reduction in the acid amount of the catalyst, and that a large reduction in the acid amount was believed to be the root cause for the superior performance of the catalyst, as the presence of a large amount of strong acid will catalyze side reactions such as cracking, which resulted in the generation of by-products such as methane and accelerated deactivation of the catalyst.

Example 1

Six hours $C_2H_4$ aromatization run was conducted at 450° C., 1bar, 0.75 g-$C_2H_4$/g-cat.hr WHSV on the catalyst 2% Ga/ZSM-5 ST-1 from the Preparation example 2 in a gas feedstock comprised of $C_2H_4$:$H_2$:$N_2$ in 1:1:1 (volume ratio) to investigate the catalyst performance at initial reaction period, which includes ethylene conversion rate, product selectivity and aromatic hydrocarbons breakdown.

Comparative example 1

Six hours $C_2H_4$ aromatization run was conducted at 450° C., 1bar, 0.75 g-$C_2H_4$/g-cat.hr WHSV on the catalyst 2% Ga/ZSM-5 from the Preparation example 1 (base catalyst) in a gas feedstock comprised of $C_2H_4$:$H_2$:$N_2$ in 1:1:1 (volume ratio) to investigate the catalyst performance at initial reaction period, which includes ethylene conversion rate, product selectivity and aromatic hydrocarbons breakdown.

Example 2

Six hours $C_2H_4$ aromatization run was conducted at 630° C., 1bar, 0.75 g-$C_2H_4$/g-cat.hr WHSV on the catalyst 2% Ga/ZSM-5 ST-1 from the Preparation example 2 in a gas feedstock comprised of $C_2H_4$:$H_2$:$N_2$ in 1:1:1 (volume ratio) to investigate the catalyst performance at initial reaction period, which includes ethylene conversion rate, product selectivity and aromatic hydrocarbons breakdown.

Comparative example 2

Six hours $C_2H_4$ aromatization run was conducted at 630° C., 1bar, 0.75 g-$C_2H_4$/g-cat.hr WHSV on the catalyst 2% Ga/ZSM-5 from the Preparation example 1 (base catalyst) in a gas feedstock comprised of $C_2H_4$:$H_2$:$N_2$ in 1:1:1 (volume ratio) to investigate the catalyst performance at initial reaction period, which includes ethylene conversion rate, product selectivity and aromatic hydrocarbons breakdown.

Example 3

Six hours $C_2H_4$ aromatization run was conducted at 550° C., 1bar, 0.75 g-$C_2H_4$/g-cat.hr WHSV on the catalyst 2%

Ga/ZSM-5 ST-1 from the Preparation example 2 in a gas feedstock comprised of $C_2H_4:H_2:N_2$ in 1:1:1 (volume ratio) to investigate the catalyst performance at initial reaction period, which includes ethylene conversion rate, product selectivity and aromatic hydrocarbons breakdown.

Comparative example 3

Six hours $C_2H_4$ aromatization run was conducted at 550° C., 1bar, 0.75 g-$C_2H_4$/g-cat.hr WHSV on the catalyst 2% Ga/ZSM-5 from the Preparation example 1 (base catalyst) in a gas feedstock comprised of $C_2H_4:H_2:N_2$ in 1:1:1 (volume ratio) to investigate the catalyst performance at initial reaction period, which includes ethylene conversion rate, product selectivity and aromatic hydrocarbons breakdown.

Example 4

Six hours $C_2H_4$ aromatization run was conducted at 475° C., 1bar, 0.75 g-$C_2H_4$/g-cat.hr WHSV on the catalyst 2% Ga/ZSM-5 ST-1 from the Preparation example 2 in a gas feedstock comprised of $C_2H_4:H_2:N_2$ in 1:1:1 (volume ratio) to investigate the catalyst performance at initial reaction period, which includes ethylene conversion rate, product selectivity and aromatic hydrocarbons breakdown.

The results are shown in Table 3.

TABLE 3

| | | Catalysts | | | | | | |
|---|---|---|---|---|---|---|---|---|
| | | Preparation example 2 (2% Ga/ZSM-5 ST-1) | | | | Preparation example 1 (2% Ga/ZSM-5) | | |
| | | Example 1 | Example 2 | Example 3 | Example 4 | Comparative Example 1 | Comparative Example 2 | Comparative Example 3 |
| | Reaction temperature, ° C. | 450 | 630 | 550 | 475 | 450 | 630 | 550 |
| | Ethylene conversion rate, % | 99.2% | 97.5% | 98.0% | 98.6% | 99.7% | 98.7% | 99.2% |
| | BTX selectivity, % | 46.6% | 65.9% | 67.9% | 52.8% | 53.4% | 54.2% | 63.6% |
| | BTX yield, % | 46.2% | 64.2% | 66.5% | 52.1% | 53.2% | 53.5% | 63.1% |
| | $CH_4$ | 3.3% | 9.0% | 8.0% | 4.2% | 6.0% | 10.7% | 11.7% |
| | $C_2H_6$ | 4.9% | 14.2% | 7.4% | 5.3% | 6.4% | 20.3% | 10.4% |
| selectivity | $C_3$ (mainly $C_3H_8$) | 18.7% | 1.9% | 9.4% | 18.0% | 22.6% | 0.6% | 3.9% |
| | $C_4$-$C_5$ | 19.5% | 0.3% | 0.9% | 13.1% | 5.3% | 0.2% | 0.3% |
| | Benzene | 8.3% | 39.1% | 27.6% | 10.7% | 13.5% | 34.5% | 32.2% |
| | Toluene | 19.6% | 22.3% | 28.7% | 22.8% | 24.7% | 17.1% | 24.8% |
| | Xylene+ ethylbenzene+ styrene (A8) | 18.7% | 4.5% | 11.5% | 19.3% | 15.2% | 2.6% | 6.7% |
| | $C_9$ aromatic hydrocarbons | 4.6% | 1.4% | 1.8% | 3.8% | 2.4% | 0.9% | 1.0% |
| | $C_{10}$+ aromatic hydrocarbons | 2.4% | 7.3% | 4.7% | 2.8% | 4.0% | 13.1% | 9.0% |
| Collective selectivity | Cracked product methane | 3.3% | 9.0% | 8.0% | 4.2% | 6.0% | 10.7% | 11.7% |
| | Recyclable fractions ($C_2$-$C_5$) | 43.1% | 16.4% | 17.7% | 36.3% | 34.3% | 21.1% | 14.7% |
| | Light aromatic hydrocarbons (A6-A9) | 51.1% | 67.3% | 69.6% | 56.6% | 55.7% | 55.1% | 64.6% |
| | Heavy aromatic hydrocarbons (A10+) | 2.4% | 7.3% | 4.7% | 2.8% | 4.0% | 13.1% | 9.0% |
| Carbon utilization (A6-A9) + (C2-C5) | | 94.3% | 83.7% | 87.3% | 92.9% | 90.0% | 76.2% | 79.2% |
| Aromatic hydrocarbon breakdown | Benzene | 15.4% | 52.4% | 37.1% | 18.0% | 22.6% | 50.6% | 43.7% |
| | Toluene | 36.6% | 30.0% | 38.6% | 38.3% | 41.3% | 25.0% | 33.6% |
| | Xylene+ ethylbenzene+ styrene (A8) | 34.9% | 6.0% | 15.5% | 32.5% | 25.4% | 3.8% | 9.1% |
| | $C_9$ aromatic hydrocarbons (A9) | 8.5% | 1.9% | 2.4% | 6.4% | 4.0% | 1.3% | 1.3% |
| | Heavy aromatic hydrocarbons (A10+) | 4.6% | 9.7% | 6.4% | 4.8% | 6.7% | 19.3% | 12.3% |

The results of Table 3 suggest that: 1) from a viewpoint of ethylene conversion rate, there was no significant change for both catalysts; 2) from a prospective of byproduct formation, steamed catalyst 2% Ga/ZSM-5 ST-1 produced less methane and ethane, indicating that less cracking reaction takes place on the catalyst; 3) among aromatic hydrocarbons product, the steamed catalyst Ga-ZSM-5 ST-1, with the exception of Example 1, produced a significantly less low value byproduct A10+ fractions, resulting in more yields of A6-A9 and higher overall carbon utilization; 4) due to the advantages mentioned above, the steamed catalyst 2%/Ga-ZSM-5 ST-1 had entirely higher BTX selectivity and yields compared to 2% Ga/ZSM-5, and could maintain higher BTX yield in a wider temperature range; due to the less methane formation, steamed catalyst 2% Ga/ZSM-5 ST-1 would be expected to outperform than the base catalyst 2%/Ga-ZSM-5 in terms of the catalyst lifetime.

Example 5

$C_2H_4$ aromatization run was conducted at 500° C., 3 bar, 1.5 g-$C_2H_4$/g-cat.hr WHSV on the catalyst 2% Ga/ZSM-5 ST-1 from the Preparation example 2 in a gas feedstock comprised of $C_2H_6$:$C_2H_4$:$H_2$:$N_2$ in 0.67:1:1:1 (volume ratio) simulating the two-step method to investigate single cycle lifetime performance of the catalyst, which includes ethylene conversion rate, liquid hydrocarbon selectivity and aromatic hydrocarbons breakdown.

Example 6

$C_2H_4$ aromatization run was conducted at 500° C., 3 bar, 1.5 g-$C_2H_4$/g-cat.hr WHSV on the catalyst 2% Ga/ZSM-5 ST-2 from the Preparation example 3 in a gas feedstock comprised of $C_2H_6$:$C_2H_4$:$H_2$:$N_2$ in 0.67:1:1:1 (volume ratio) simulating the two-step method to investigate single cycle lifetime performance of the catalyst, which includes ethylene conversion rate, liquid hydrocarbon selectivity and aromatic hydrocarbons breakdown.

Example 7

$C_2H_4$ aromatization run was conducted at 500° C., 3 bar, 1.5 g-$C_2H_4$/g-cat.hr WHSV on the catalyst 2% Ga/ZSM-5 ST-3 from the Preparation example 4 in a gas feedstock comprised of $C_2H_6$:$C_2H_4$:$H_2$:$N_2$ in 0.67:1:1:1 (volume ratio) simulating the two-step method to investigate single cycle lifetime performance of the catalyst, which includes ethylene conversion rate, liquid hydrocarbon selectivity and aromatic hydrocarbons breakdown.

Comparative example 4

$C_2H_4$ aromatization run was conducted at 500° C., 3 bar, 1.5 g-$C_2H_4$/g-cat.hr WHSV on the catalyst 2% Ga/ZSM-5 from the Preparation example 1 in a gas feedstock comprised of $C_2H_6$:$C_2H_4$:$H_2$:$N_2$ in 0.67:1:1:1 (volume ratio) simulating the two-step method to investigate single cycle lifetime performance of the catalyst, which includes ethylene conversion rate, liquid hydrocarbon selectivity and aromatic hydrocarbons breakdown.

Figure 2A:
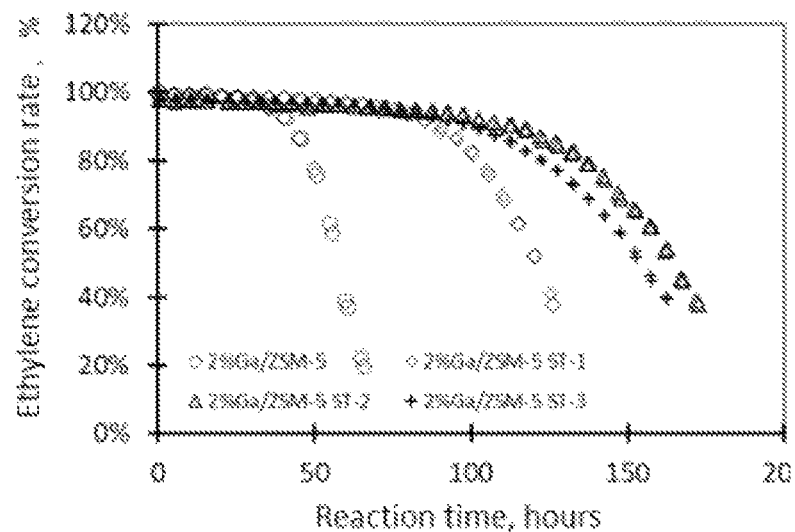
Figure 2B:
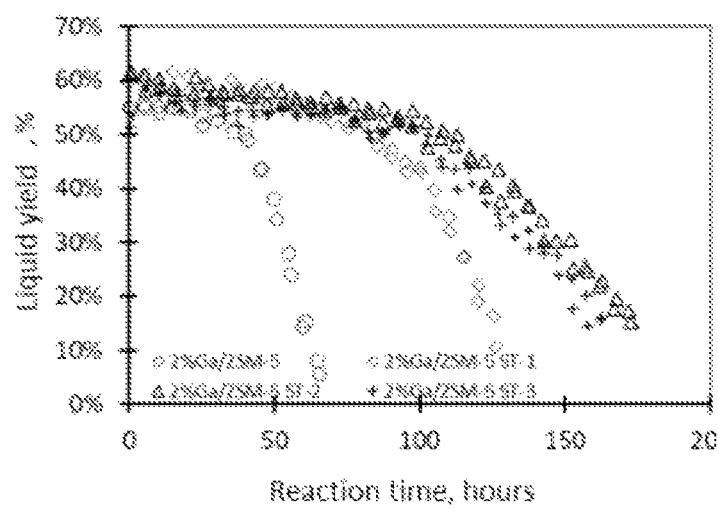
Figure 2C:
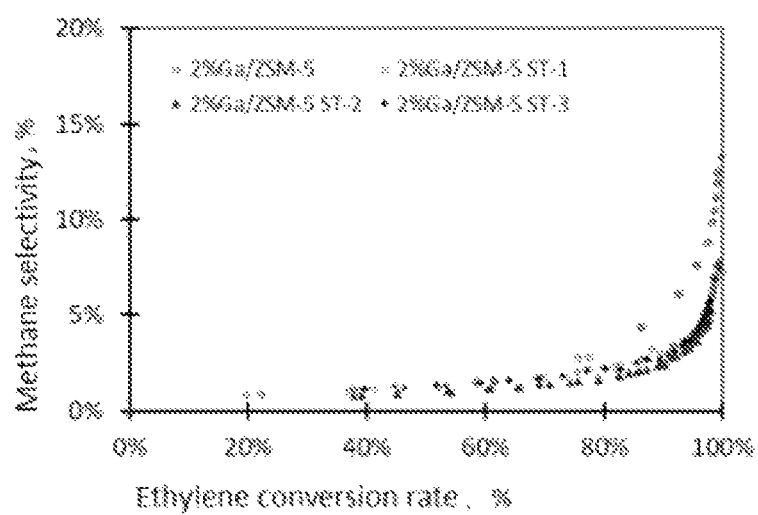
Figure 2D:
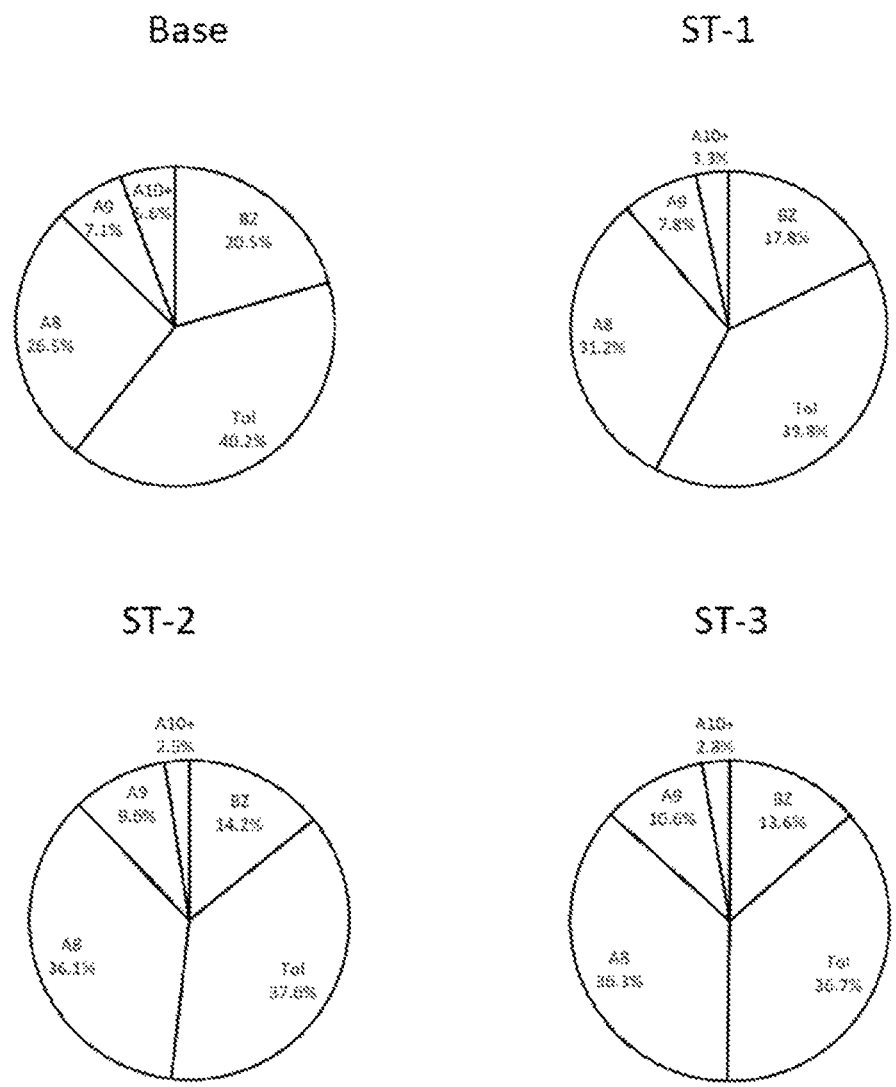

The above described lifetime run results are plotted in FIG. 2A-2D, wherein FIG. 2A shows the ethylene conversion rate, FIG. 2B illustrates the liquid product ($C_6^+$, hereinafter referred to as "the liquid state HC") yield, FIG. 2C illustrates the ethylene conversion rate versus methane selectivity, FIG. 2D shows breakdown of the aromatic hydrocarbon fractions.

As can be seen from the results in FIGS. 2A-2D, the three groups of steamed catalysts showed excellent lifetime performance. The total run time of the steamed catalysts was almost 2-3 times that of the base catalyst. The liquid hydrocarbon yields of all the catalysts did not have large difference in the initial stages, but the steamed catalysts maintained high yields for a much longer time. As illustrated in FIG. 2C, in the case of the same ethylene conversion rate, the methane selectivity of steamed catalysts was significantly lower than that of the base catalyst. This is also the root cause for the catalysts to have longer cycle lifetime and higher liquid hydrocarbon yields. Furthermore, it can be discovered from a careful analysis of the aromatic hydrocarbon fraction breakdown that the content of heavy aromatic hydrocarbons (A10+) on steamed catalysts is about 50% lower than that of the base catalyst.

As can be seen from the above, the performance of the steamed catalyst has significant advantages over the base catalyst in terms of ethylene conversion rate, lifetime, liquid hydrocarbon yield, and production amount of the pyrolysis product, methane.

In regard to the abovementioned single cycle lifetime experiments, BTX production capacity was calculated by using equation (1). The lower time limit of the calculation was that the ethylene conversion rate drops to 80%. The results were shown in Table 4.

BTX production capacity (g-BTX/g-catalyst.cycle)=run time (hr) with ethylene yield down to 80%*liquid hydrocarbon yield (%)*percentage of BTX in total liquid hydrocarbons (%)*WHSV for $C_2H_4$ (g-$C_2H_4$/g-cat. hr)----equation (1)

TABLE 4

| | Catalysts | BTX production capacity, g-BTX/g-cat.cycle | Incremental quantity, % |
|---|---|---|---|
| Example 5 | Preparation example 2 (2% Ga/ZSM-5 ST-1) | 75.4 | 130% |
| Example 6 | Preparation example 3 (2% Ga/ZSM-5 ST-2) | 93.4 | 185% |
| Example 7 | Preparation example 4 (2% Ga/ZSM-5 ST-3) | 84.2 | 157% |
| Comparative example 4 | Preparation example 1 (2% Ga/ZSM-5) | 32.7 | Base |

The data in Table 4 shows that each of the three groups of steamed catalysts has obtained higher BTX production capacity, with an increase of 130-185% over the base catalyst.

Example 8

$C_2H_4$ aromatization run was conducted at 450° C., 1bar, 0.5 g-$C_2H_4$/g-cat.hr WHSV on the catalyst 2% Ga/ZSM-5 ST-3 from the Preparation example 4 in a simple gas feedstock comprised of $C_2H_4$:$H_2$:$N_2$ in 1:1:1.67 (volume ratio) to investigate single cycle lifetime performance of the catalyst, which includes ethylene conversion rate, liquid hydrocarbon selectivity, methane selectivity and aromatic hydrocarbons breakdown, and the BTX production capacity was calculated. The results were shown in FIG. 3 and Table 5.

Comparative example 5

$C_2H_4$ aromatization run was conducted at 450° C., 1bar, 0.5 g-$C_2H_4$/g-cat.hr WHSV on the catalyst 2% Ga/ZSM-5 from the Preparation example 1 in a simple gas feedstock comprised of $C_2H_4$:$H_2$:$N_2$ in 1:1:1.67 (volume ratio) to investigate single cycle lifetime performance of the catalyst, which includes ethylene conversion rate, liquid hydrocarbon selectivity, methane selectivity and aromatic hydrocarbons breakdown, and the BTX production capacity was calculated. The results were shown in FIG. 3 and Table 5.

Figure 3:
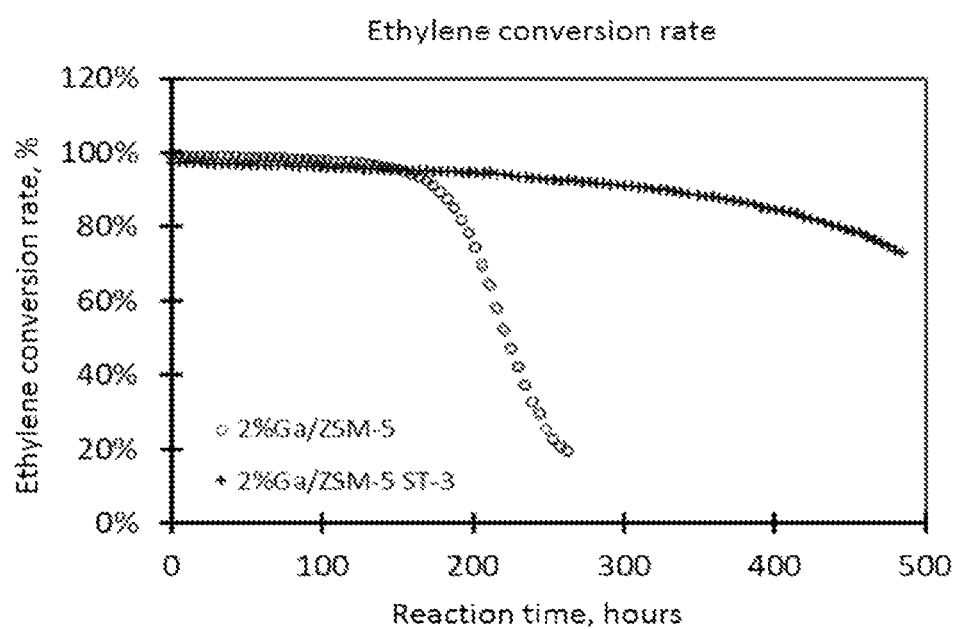
FIG. 3 illustrates the cycle lifetime results obtained for Example 8 and Comparative Example 5 at 450° C., 1 bar, WHSV=0.5 g-$C_2H_4$/g-cat.hr, and the gas feedstock comprised of $C_2H_4$:$H_2$:$N_2$ in 1:1:1.67 (volume ratio).

As can be seen from the conversion rate curves in FIG. 3 and the results of Table 5, the improvement in catalyst lifetime and the like from the steaming treatment is also significant under such a condition.

Example 9

$C_2H_4$ aromatization run was conducted at 450° C., 1bar, 0.5 g-$C_2H_4$/g-cat.hr WHSV on the catalyst 4% Ga/ZSM-5 ST-3 from the Preparation example 6 in a simple gas feedstock comprised of $C_2H_4$:$H_2$:$N_2$ in 1:1:1.67 (volume ratio) to investigate single cycle lifetime performance of the catalyst, which includes ethylene conversion rate, liquid hydrocarbon selectivity, methane selectivity and aromatic hydrocarbons breakdown, and the BTX production capacity was calculated. The results were shown in FIG. 4 and Table 5.

Comparative example 6

$C_2H_4$ aromatization run was conducted at 450° C., 1bar, 0.5 g-$C_2H_4$/g-cat.hr WHSV on the catalyst 4% Ga/ZSM-5 from the Preparation example 5 in a simple gas feedstock comprised of $C_2H_4$:$H_2$:$N_2$ in 1:1:1.67 (volume ratio) to investigate single cycle lifetime performance of the catalyst, which includes ethylene conversion rate, liquid hydrocarbon selectivity, methane selectivity and aromatic hydrocarbons breakdown, and the BTX production capacity was calculated. The results were shown in FIG. 4 and Table 5.

Figure 4:
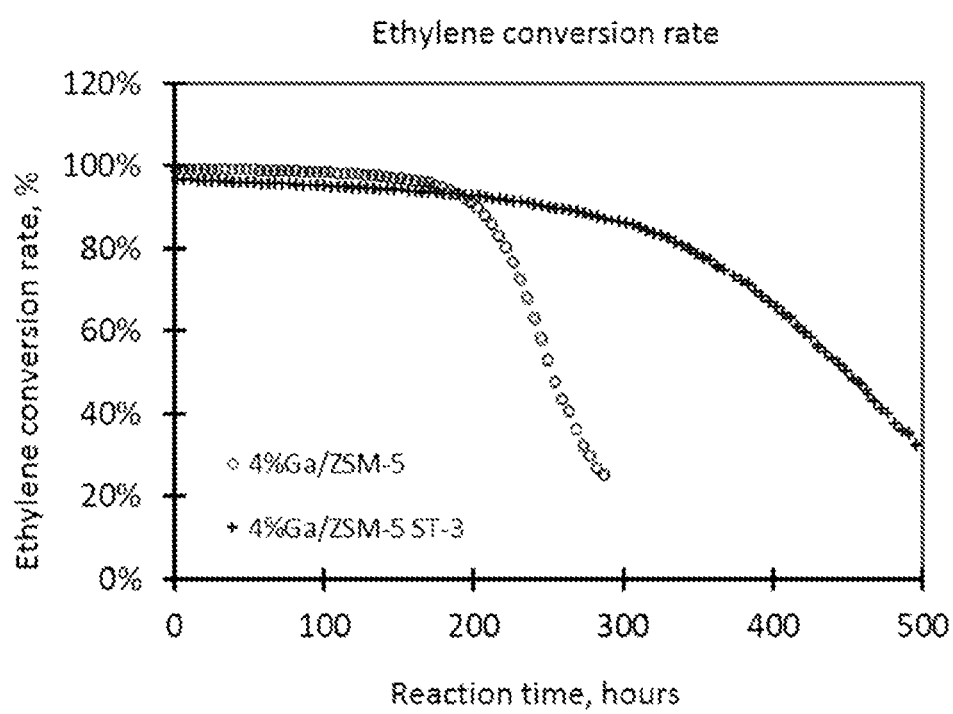
FIG. 4 illustrates the cycle lifetime results obtained for Example 9 and Comparative Example 6 at 450° C., 1 bar, WHSV=0.5 g-$C_2H_4$/g-cat.hr, and the gas feedstock comprised of $C_2H_4$:$H_2$:$N_2$ in 1:1:1.67 (volume ratio).

As can be seen from the conversion rate curves in FIG. 4 and the results of Table 5, the steaming treatment was also effective for improving the lifetime and the like of the 4% Ga catalyst, but the percent increase was lower than that of 2% Ga.

TABLE 5

|  | Catalysts | BTX production capacity, g-BTX/g-cat.cycle | Incremental quantity, % |
| --- | --- | --- | --- |
| Example 8 | Preparation example 4 (2% Ga/ZSM-5 ST-3) | 83.5 | 72% |
| Comparative example 5 | Preparation example 1 (2% Ga/ZSM-5) | 48.5 | Base |
| Example 9 | Preparation example 6 (4% Ga/ZSM-5 ST-3) | 76.2 | 32% |
| Comparative example 6 | Preparation example 5 (4% Ga/ZSM-5) | 57.7 | Base |

The above content describes in detail the preferred embodiments of the present disclosure, but the present disclosure is not limited thereto. A variety of simple modifications can be made in regard to the technical solutions of the present disclosure within the scope of the technical concept of the present disclosure, including a combination of individual technical features in any other suitable manner, such simple modifications and combinations thereof shall also be regarded as the content disclosed by the present disclosure, each of them falls into the protection scope of the present disclosure.

What is claimed is:

1. A catalyst comprising an acidic molecular sieve and an olefin aromatization active metal component, wherein a total acid amount of the catalyst as measured by $NH_3$-TPD method is not higher than 0.35 mmol/g, and a ratio of strong acid amount to weak acid amount is within a range of 0.8-1.2.

2. The catalyst of claim 1, wherein the total acid amount of the catalyst is 0.1-0.3 mmol/g, and the ratio of strong acid amount to weak acid amount is within a range of 0.9-1.1.

3. The catalyst of claim 1, wherein the strong acid amount of the catalyst is within a range of 0.05-0.2 mmol/g, and the weak acid amount is within a range of 0.05-0.2 mmol/g; and/or
the catalyst has a desorption temperature for $NH_3$ of lower than 370° C. at a strong acid site, and lower than 235° C. at a weak acid site.

4. The catalyst of claim 3, wherein the strong acid amount of the catalyst is within a range of 0.06-0.15 mmol/g, and the weak acid amount is within a range of 0.06-0.15 mmol/g; and/or
the desorption temperature of $NH_3$ is within a range of 340-365° C. at the strong acid site, and 220-230° C. at the weak acid site of the catalyst respectively.

5. The catalyst of claim 1, wherein the acidic molecular sieve is a molecular sieve with a MFI structure; and the olefin aromatization active metal component is Ga; and/or
a weight ratio of the acidic molecular sieve to the olefin aromatization active metal component is 1:0.001-0.1.

6. The catalyst of claim 5, wherein the acidic molecular sieve is ZSM-5.

7. The catalyst of claim 1, wherein the catalyst further comprises a binder in an amount of 10-40 wt % based on a total amount of the catalyst.

8. The catalyst of claim 7, wherein the amount of the binder is 15-25 wt % based on the total amount of the catalyst; and/or the binder is one or more selected from the group consisting of silica, alumina, silicon carbide, clay, ceria, lanthana, magnesium oxide, titanium oxide and zirconia.

* * * * *